US007662993B2

(12) United States Patent
Alvarez et al.

(10) Patent No.: US 7,662,993 B2
(45) Date of Patent: Feb. 16, 2010

(54) SYNTHESIS OF [$^{13}$C] AND [$^{2}$H] SUBSTITUTED METHACRYLIC ACID, [$^{13}$C] AND [$^{2}$H] SUBSTITUTED METHYL METHACRYLATE AND/OR RELATED COMPOUNDS

(75) Inventors: Marc A. Alvarez, Santa Fe, NM (US); Rodolfo A. Martinez, Santa Fe, NM (US); Clifford J. Unkefer, Los Alamos, NM (US)

(73) Assignee: Los Alamos National Security, LLC, Los Alamos, NM (US)

( * ) Notice: Subject to any disclaimer, the term of this patent is extended or adjusted under 35 U.S.C. 154(b) by 0 days.

(21) Appl. No.: 11/591,828

(22) Filed: Nov. 2, 2006

(65) Prior Publication Data

US 2007/0191635 A1    Aug. 16, 2007

(51) Int. Cl.
C07C 317/12 (2006.01)
C07C 321/22 (2006.01)

(52) U.S. Cl. .................. 562/427; 562/426; 562/429; 560/9; 560/11

(58) Field of Classification Search ............ None
See application file for complete search history.

(56) References Cited

U.S. PATENT DOCUMENTS

| 6,713,044 B2* | 3/2004 | Martinez et al. ......... 424/1.81 |
| 2003/0158445 A1* | 8/2003 | Martinez et al. ......... 568/28 |
| 2006/0178534 A1* | 8/2006 | Martinez et al. ......... 564/152 |
| 2007/0106085 A1* | 5/2007 | Alvarez et al. ......... 560/11 |
| 2007/0191635 A1* | 8/2007 | Alvarez et al. ......... 562/423 |

OTHER PUBLICATIONS

Tsukurimichi et al. Pyrolysis of ⊐-acyl substituted ethyl phenyl sulfoxide. Phosphorus, Sulfur and Silicon and the Related Elements (1989), 46(3-4), 113-20.*
Tsukurimichi et al. Phosphorus, Sulfur and Silicon and the related elements 1989, 46,113-20; CAPLUS abstract.*
Barbieri et al. Journal of the chemical society [Section] C: Organic Chemistry, 1968, 6, 659-668; CAPLUS abstract.*
Kato et al Tetrahedron asymmetry 2004, 15, 2965-2973.*
Aitken et al. Journal of the Chemical society, Perkin Transactions 1: Organic and Bio-organic chemistry 1999, 5, 593-604; CAPLUS abstract.*
Piechulek et al. Roczniki Chemii 1933, 13, 520-529; CAPLUS abstract.*
Pedrosa et al. Synthesis 2004 10, 1629-1632; CAPLUS abstract.*
Lemaire et al. European Journal of Organic Chemistry 2004, 13, 2840-2847; CAPLUS abstract.*
Spinelli et al., "On the Reaction of 3-Bromo-2nitrobenzo[b]thiophene $^{13}$C-Labeled at C-2 with 3-(Trifluoromethyl)aniline: A Preliminary Insight into a Nucleophilic Substitution with Rearrangement," J. Org. Chem 1997, 62, 4921-4923, (1997).

* cited by examiner

Primary Examiner—Daniel M Sullivan
Assistant Examiner—Yevegeny Valenrod
(74) Attorney, Agent, or Firm—Bruce H. Cottrell

(57) ABSTRACT

The present invention is directed to labeled compounds of the formulae

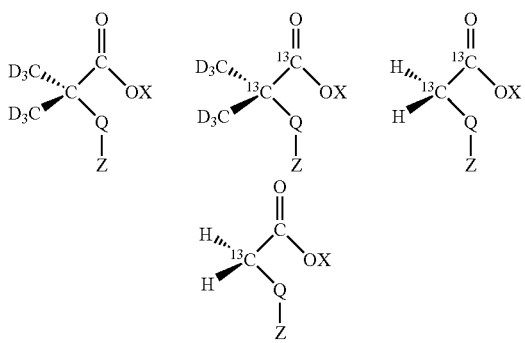

wherein Q is selected from the group consisting of —S(=O)—, and —S(=O)$_2$—, Z is selected from the group consisting of 1-naphthyl, substituted 1-naphthyl, 2-naphthyl, substituted 2-naphthyl, and phenyl groups with the structure

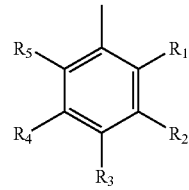

wherein $R_1$, $R_2$, $R_3$, $R_4$ and $R_5$ are each independently selected from the group consisting of hydrogen, a $C_1$-$C_4$ lower alkyl, a halogen, and an amino group selected from the group consisting of $NH_2$, NHR and NRR' where R and R' are each independently selected from the group consisting of a $C_1$-$C_4$ lower alkyl, an aryl, and an alkoxy group, and X is selected from the group consisting of hydrogen, a $C_1$-$C_4$ lower alkyl group, and a fully-deuterated $C_1$-$C_4$ lower alkyl group.

16 Claims, 2 Drawing Sheets

US 7,662,993 B2

SYNTHESIS OF [$^{13}$C] AND [$^2$H] SUBSTITUTED METHACRYLIC ACID, [$^{13}$C] AND [$^2$H] SUBSTITUTED METHYL METHACRYLATE AND/OR RELATED COMPOUNDS

STATEMENT REGARDING FEDERAL RIGHTS

This invention was made with government support under Contract No. W-7405-ENG-36 awarded by the U.S. Department of Energy. The government has certain rights in the invention.

FIELD OF THE INVENTION

The present invention relates to labeled compounds and more particularly to compounds labeled with carbon-13 and hydrogen-2. More particularly, the present invention relates intermediates useful in the preparation of [$^{13}$C$_{1-5}$]methacrylic acid, [$^{13}$C$_{1-5}$, $^2$H$_5$]methacrylic acid, [$^2$H$_5$]methacrylic acid, [$^{13}$C$_{1-5}$]methyl methacrylate, [$^{13}$C$_{1-5}$, $^2$H$_5$]methyl methacrylate, [$^{13}$C$_{1-6}$, $^2$H$_8$]methyl methacrylate, [$^2$H$_5$]methyl methacrylate, [$^2$H$_8$]methyl methacrylate, and the like.

BACKGROUND OF THE INVENTION

The use of fully deuterated methacrylic acid for preparation of polyacrylic acid and subsequent preparation of optical fibers from such polyacrylic acid has been demonstrated to give an enhancement in the transmission distances of the optical fibers. Hence, a cost effective method for the production of large quantities of deuterated methacrylic acid is desirable. Currently, the starting material of [$^2$H$_5$]methacrylic acid is produced from [$^2$H$_6$]acetone and cyanide. The [$^2$H$_6$]acetone is produced by exchange with deuterium oxide which makes the production of large quantities of that material extremely expensive.

The development of alternative routes for the production of [$^2$H$_5$]methacrylic acid from D$_2$ could lower the costs. Additionally, the development of routes for the production of [$^2$H$_8$]methyl methacrylate is desirable.

SUMMARY OF THE INVENTION

In accordance with the purposes of the present invention, as embodied and broadly described herein, the present invention provides selected labeled compounds of the formulae

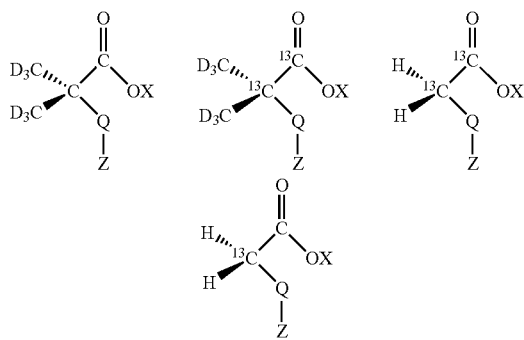

wherein Q is selected from the group consisting of —S—, —S(=O)—, and —S(=O)$_2$—, Z is selected from the group consisting of 1-naphthyl, substituted 1-naphthyl, 2-naphthyl, substituted 2-naphthyl, and phenyl groups with the structure

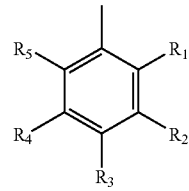

wherein R$_1$, R$_2$, R$_3$, R$_4$ and R$_5$ are each independently selected from the group consisting of hydrogen, a C$_1$-C$_4$ lower alkyl, a halogen, and an amino group selected from the group consisting of NH$_2$, NHR and NRR' where R and R' are each independently selected from the group consisting of a C$_1$-C$_4$ lower alkyl, an aryl, and an alkoxy group, and X is selected from the group consisting of hydrogen, a C$_1$-C$_4$ lower alkyl group, and a fully-deuterated C$_1$-C$_4$ lower alkyl group. In one preferred embodiment, X is methyl.

The present invention further provides a process of preparing [$^{13}$C]methacrylic acid by reacting a (CH$_3$CH$_2$O—$^{13}$C(O)—$^{13}$CH$_2$)-aryl sulfone precursor with $^{13}$CHI to form a (CH$_3$CH$_2$O—$^{13}$C(O)—$^{13}$C($^{13}$CH$_3$)$_2$)-aryl sulfone intermediate; and, reacting the (CH$_3$CH$_2$O—$^{13}$C(O)—$^{13}$C($^{13}$CH$_3$)$_2$)-aryl sulfone intermediate with sodium hydroxide, followed by reaction with an acid such as hydrochloric acid to form [$^{13}$C]methacrylic acid.

The present invention further provides a process of preparing [$^2$H$_8$]methyl methacrylate by reacting a (HOOC—C(C$^2$H$_3$)$_2$)-aryl sulfinyl intermediate with CD$_3$I to form a ($^2$H$_3$COOC—C(C$^2$H$_3$)$_2$)— aryl sulfinyl intermediate, and heating the ($^2$H$_3$COOC—C(C$^2$H$_3$)$_2$)-aryl sulfinyl intermediate at temperatures and for time sufficient to form [$^2$H$_8$] methyl methacrylate.

BRIEF DESCRIPTION OF THE DRAWINGS

FIG. 2 shows the conversion of phenylthio-[1,2-$^{13}$C$_2$] acetic acid to phenylsulfinyl-[1,2-$^{13}$C$_2$]acetic acid and phenylsulfonyl-[1,2-$^{13}$C$_2$]acetic acid.

DETAILED DESCRIPTION

Figure 1:
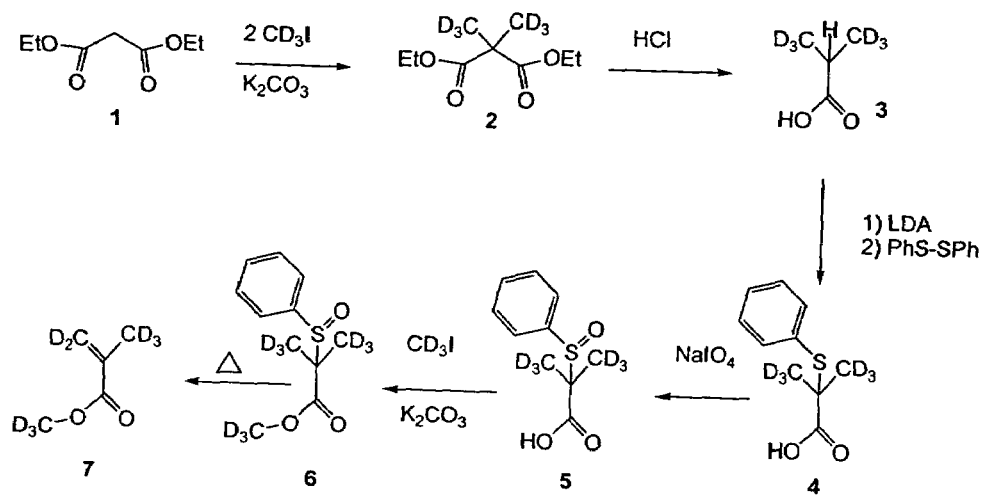
FIG. 1 shows a synthetic route to 2-[$^2$H$_3$]methyl-2-propenoic [3,3-$^2$H$_2$]acid, —[$^2$H$_3$]methyl ester (or [$^2$H$_8$]methyl methacrylate) through the intermediate compounds of diethyl [$^2$H$_6$]dimethylmalonate, [3,3,3,3',3',3'-$^2$H$_6$]isobutyric acid, 2-[$^2$H$_3$]methyl-2-(phenylthio)-[3,3,3-$^2$H$_3$]propionoic acid, 2-[$^2$H$_3$]methyl-2-(phenylsulfinyl)-[3,3,3-$^2$H$_3$]propionoic acid, and 2-[$^2$H$_3$]methyl-2-(phenylsulfinyl)-[3,3,3-$^2$H$_3$]propionoic acid [$^2$H$_3$]methyl ester.

The present invention is concerned with various labeled compounds, and especially to certain labeled methylacrylic acids and methyl methacrylates. Further, the present invention is concerned with processes of preparing such labeled compounds.

As used herein, the term "aryl" means a monovalent monocyclic or bicyclic aromatic hydrocarbon radical of 6 to 10 ring atoms, and optionally substituted independently with one, two, three, four or five substituents selected from alkyl, haloalkyl, cycloalkyl, halo, nitro, cyano, —OR (where R is hydrogen, alkyl, haloalkyl, cycloalkyl, optionally substituted phenyl), acyl, and —COOR (where R is hydrogen or alkyl). More specifically, the term "aryl" includes, but is not limited to 1-naphthyl, substituted 1-naphthyl, 2-naphthyl, substituted 2-naphthyl, and phenyl groups with the structure

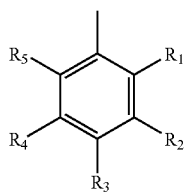

wherein $R_1$, $R_2$, $R_3$, $R_4$ and $R_5$ are each independently hydrogen, a lower alkyl, i.e., a $C_1$-$C_4$ alkyl such as methyl, ethyl, n-propyl, iso-propyl, butyl, isobutyl, and tert-butyl, a halogen such as chloro, bromo or iodo, an amino group such as $NH_2$, NHR or NRR' where R and R' are each independently a lower alkyl or an aryl as described above, or an alkoxy group such as O-alkyl or O-aryl where the alkyl is a lower alkyl as described above or an aryl as described above. By "substituted" is meant that the naphthyl group can include one or more substituents in place of a hydrogen atom, such substituents including the same as described for $R_1$-$R_5$.

As used herein, the term "[$^{13}$C, $^2$H$_n$]" means the particular compound includes a $^{13}$C label and deuterium atoms in place of n number of hydrogens. The present invention provides a process of preparing labeled compounds as described wherein the resultant product includes one or more of the desired labels, i.e., $^{13}$C and/or $^2$H, at an abundance level detectably greater than its natural abundance. Similarly, the labeled compounds of the present invention include one or more of the desired labels, i.e., $^{13}$C and/or $^2$H, at an abundance level detectably greater than its natural abundance.

The present invention provides labeled compounds of the formulae

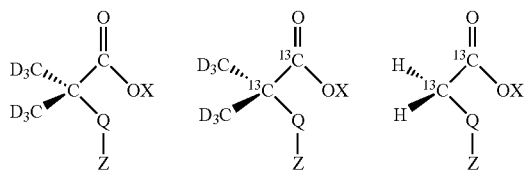

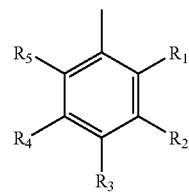

wherein Q is selected from the group consisting of —S—, —S(=O)—, and —S(=O)$_2$—, Z is an aryl group selected from the group consisting of 1-naphthyl, substituted 1-naphthyl, 2-naphthyl, substituted 2-naphthyl, and phenyl groups with the structure

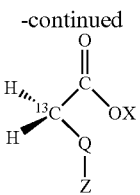

wherein $R_1$, $R_2$, $R_3$, $R_4$ and $R_5$ are each independently selected from the group consisting of hydrogen, a $C_1$-$C_4$ lower alkyl, a halogen, and an amino group selected from the group consisting of $NH_2$, NHR and NRR' where R and R' are each independently selected from the group consisting of a $C_1$-$C_4$ lower alkyl, an aryl, and an alkoxy group, and X is selected from the group consisting of hydrogen, a $C_1$-$C_4$ lower alkyl group, and a fully-deuterated $C_1$-$C_4$ lower alkyl group. Such labeled materials can be attractive for a variety of applications, especially for the preparation of 2-[$^2$H$_3$]methyl-2-propenoic-[3,3-$^2$H$_2$] acid [$^2$H$_3$]methyl-ester (sometimes known as [$^2$H$_8$]methyl methacrylate or [$^2$H$_3$]methyl [$^2$H$_5$] methacrylate) and for the preparation of 2-[$^2$H$_3$]methyl-2-propenoic-[3,3-$^2$H$_2$] acid (sometimes known as [$^2$H$_5$]methacrylic acid). These deuterated methacrylic acid and deuterated methyl methacrylate are useful in the preparation of deuterated polyacrylates. Further, [$^{13}$C, $^2$H$_8$]- and [$^2$H$_8$]-labeled materials can be attractive for application in metabolism studies and for mass tagging of polymers and monomers. Various combinations of $^{13}$C and $^2$H labeling can be accomplished by the teachings of the present invention.

Throughout the present description, the group referred to as sulfide (also referred to as thio) can also be represented by —S—. The group referred to as sulfinyl can also be represented by —S(=O)—. The group referred to as sulfone can also be represented by —S(=O)$_2$—. Generally, where one of the particular sulfur groups is described, such as sulfide, the processes may be carried out with the other sulfur groups, such as sulfinyl or sulfone.

The present invention also provides efficient processes for the preparation of virtually any $^2$H and/or $^{13}$C containing isotopomers of methacrylic acid and methyl methacrylate.

In one embodiment, a process of preparing [$^2$H$_8$]methyl methacrylate includes reacting a (HOOC—C(C$^2$H$_3$)$_2$— aryl sulfinyl intermediate with CD$_3$I to form a ($^2$H$_3$COOC—C(C$^2$H$_3$)$_2$)— aryl sulfinyl intermediate, and heating the ($^2$H$_3$COOC—C(C$^2$H$_3$)$_2$)-aryl sulfinyl intermediate at temperatures and for time sufficient to form [$^2$H$_8$]methyl methacrylate The present invention is more particularly described in the following examples, which are intended as illustrative only, since numerous modifications and variations will be apparent to those skilled in the art.

Example 1

Synthesis of diethyl [$^2$H$_6$]dimethylmalonate (compound 2 in FIG. 1) was as follows. Diethyl malonate (10 g, 0.0624 moles) was dissolved into dimethylformamide (DMF) (120 mL) and to this solution, potassium carbonate (25.9 g, 0.1873 moles) was added. The reaction was stirred at room temperature for 1 hour and then [$^2$H$_3$]methyl iodide (18.2 g, 0.128 moles) was added to the mixture. The reaction was stirred for 4 days and then filtered to remove the excess potassium carbonate and potassium iodide. The red DMF solution was then treated with aqueous sodium thiosulfate (5% by wt) (100 mL). This solution was extracted with portions of ethyl acetate (3×250 mL) and the ethyl acetate layer was dried over sodium sulfate. The solvent was removed and a 1:1 mixture of the diethyl [$^2$H$_6$]dimethylmalonate and DMF was isolated. The yield was calculated (by NMR) to be 92%.

Synthesis of [3,3,3,3',3',3'-$^2$H$_6$]isobutyricacid (compound 3 in FIG. 1) was as follows. The 1:1 mixture of diethyl [$^2$H$_6$]dimethylmalonate (compound 2 in FIG. 1) was suspended into hydrochloric acid (12N, 75 mL) and heated to reflux for 24 hours. After this period the reaction was diluted into 75 mL of water and then extracted with portions of dichloromethane (4×100 mL). The organic layer was then dried over sodium sulfate and evaporated to give 2.3 g of the [3,3,3,3',3',3'-$^2$H$_6$]isobutyric acid.

Synthesis of 2-[$^2$H$_3$]methyl-2-(phenylthio)-[3,3,3-$^2$H$_3$]propionoic acid, (compound 4 in FIG. 1) was as follows. [3,3,3,3',3',3'-$^2$H$_6$]Isobutyric acid (9.72 g, 0.1033 moles) was dissolved into tetrahydrofuran (THF) (200 mL) and cooled in an ice bath. To this mixture, lithium diisopropyl amide (1.5M, 151 mL, 0.2272 moles) was added slowly. After 30 minutes, diphenyl disulfide (24.81 g, 0.1136 moles) was added as a solution in THF (100 mL). The reaction was allowed to warm to room temperature and then stirred overnight. The reaction mixture was poured into water (300 mL) and then extracted with portions of ethyl acetate (3×100 mL). The pH of the aqueous solution was adjusted to pH=7.5 with hydrochloric acid (1M) and then extracted again with portions of ethyl acetate (3×100 mL). The pH of the aqueous was then adjusted to 2.5 with hydrochloric acid (1N) and extracted with portions of ethyl acetate (3×150 mL). The organic layer was dried with sodium sulfate and then evaporated to give 19.01 g (91%) of the 2-[$^2$H$_3$]methyl-2-(phenylthio)-[3,3,3-$^2$H$_3$]propionoic acid. The product was suitable for use in the next step without purification.

Synthesis of 2-[$^2$H$_3$]methyl-2-(phenylsulfinyl)-[3,3,3-$^2$H$_3$]propionoic acid, (compound 5 in FIG. 1) was as follows. 2-[$^2$H$_3$]methyl-2-(phenylthio)-[3,3,3-$^2$H]propionoic acid, (compound 4 in FIG. 1) (2.5 g, 0.0127 moles) was dissolved into methanol:water (1:1 v/v 37.5 mL) and to this mixture sodium periodate (3.00 g, 0.014 moles) was add as a solid. The reaction was stirred for 3 hours at room temperature and then filtered to remove solids. The solution was evaporated to remove most of the methanol and then extracted with portions of dichloromethane (4×100 mL). The organic layer was dried and evaporated to yield the [3,3,3-$^2$H$_3$]propionic acid, 2-[$^2$H$_3$]methyl-2-(phenylsulfinyl)-(2.5 g 92%). The product was suitable for use in the next step without purification.

Synthesis of 2-[$^2$H$_3$]methyl-2-(phenylsulfinyl)-[3,3,3-$^2$H$_3$]propionoic acid, methyl ester (compound 6 in FIG. 1) was as follows. 2-[$^2$H$_3$]methyl-2-(phenylsulfinyl)-[3,3,3-$^2$H$_3$]Propionic acid, (12 g, 0.059 moles) was dissolved into dimethylformamide (24 mL). Potassium carbonate (8.98 g, 0.065 moles) was added to the reaction. The mixture was allowed to stir for 15 minutes and then [$^2$H$_3$]methyl iodide (2.29 g, 0.065 moles) was added neat. The reaction was stirred for 1 hour and then quenched with hydrochloric acid (1N, 20 mL). The reaction was extracted with portions of dichloromethane (3×50 mL) and then the organic was dried over sodium sulfate then evaporated to give a yellow oil which contained only a trace of DMF and pure product. The DMF was removed by vacuum at 50° C. which left only the pure 2-[$^2$H$_3$]methyl-2-(phenylsulfinyl)-[3,3,3-$^2$H$_3$]propionic acid, methyl ester (12.99 g, 99.8%) which was suitable for use in the next step without purification.

Synthesis of 2-[$^2$H$_3$]methyl-2-[3,3-$^2$H$_2$]propenoic acid [$^2$H$_3$]methyl ester (compound 7 in FIG. 1) was as follows. The solid 2-[$^2$H$_3$]methyl-2-(phenylsulfinyl)-[3,3,3-$^2$H$_3$]propionic acid methyl ester (5 g, 0.021 moles) was slowly heated to 100° C. under vacuum and the 2-[$^2$H$_3$]methyl-2-[3,3-$^2$H$_2$]propenoic-acid [$^2$H$_3$]methyl ester was collected by using a dry ice trap. The reaction was heated until the product stopped distilling over. The product (2.15 g, 93%) contained approximately 2 percent water. This water was removed by distillation from calcium hydride. The yield after this step was 85%.

Example 2

The synthesis of phenylthio-[1,2-$^{13}$C$_2$]acetic acid (compound 9 in FIG. 2) was as follows. A round-bottomed flask (1000 ml) was equipped with a rubber septum and a magnetic stir bar and placed under an argon atmosphere. In the flask, the [1-$^{13}$C]methyl phenyl sulfide (compound 8 in FIG. 2) (30.0 g, 0.240 mol) was dissolved in freshly distilled tetrahydrofuran (450 ml). The flask was cooled to −78° C. with a dry ice/ethanol bath. To this solution, sec-butyllithium (188 ml, 0.264 mol) was added drop wise over 10 minutes. The solution was stirred for 30 min at −78° C. The $^{13}$CO$_2$ (5.4 g, 0.120 mol) was placed in a stainless steel lecture bottle (250 ml) which was attached to the pressure/vacuum manifold. The reaction flask was attached to the manifold and evacuated. $^{13}$CO$_2$ was introduced into the reaction vessel over a few minutes so that the pressure in the flask does not exceed 760 mm. After the addition of the $^{13}$CO$_2$, the reaction was stirred for 1 hr at −78° C. then stirring was continued as the reaction was allowed to warm to room temperature (2 hrs). The reaction was quenched with the addition of water (100 ml), the aqueous layer was extracted with portions of ethyl acetate (3×100 ml). Then pH of the aqueous layer was then acidified using an aqueous solution of hydrochloric acid (6N) to pH 2.0. The aqueous layer was then extracted with portions of ethyl acetate (3×200 ml). The organic layer was dried with solid sodium sulfate and the solvent removed in vacuo. Volatile compounds were removed from the resulting oil under vacuumed. The resulting yellowish solid was phenylthio-[1,2-$^{13}$C]acetic acid (18.95 g, 93%).

Figure 2:
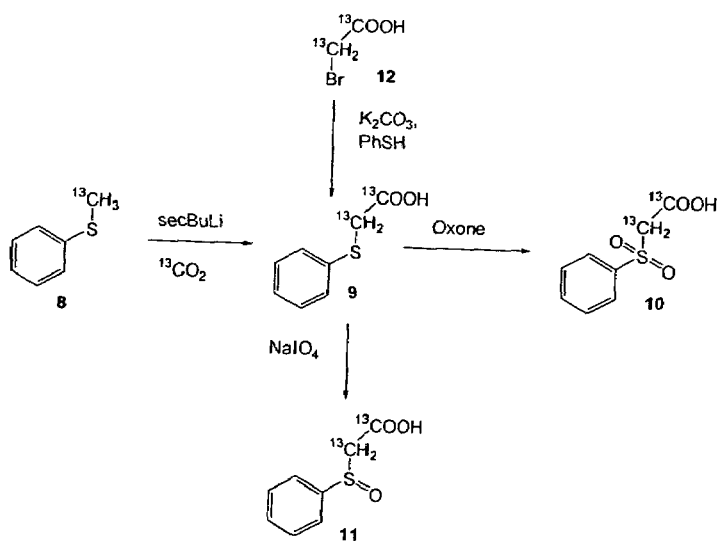
FIG. 2 shows two synthetic routes to phenylthio-[1,2-$^{13}$C$_2$] acetic acid from either [$^{13}$C]methyl phenyl sulfide and $^{13}$C] carbon dioxide or from bromo-[1,2-$^{13}$C$_2$]acetic acid. In addition

Alternatively, phenylthio-[1,2-$^{13}$C$_2$]acetic acid (compound 9 in FIG. 2) was prepared from bromo-[1,2-$^{13}$C$_2$] acetic acid (compound 12 in FIG. 2). A separate round-bottom flask was charged with a solution containing NaOH (1.56 g, 0.039 moles), H$_2$O (50 ml) and ethanol. The flask was sealed with a rubber septum and stirred at room temperature. The benzenethiol (4.29 g, 0.039 moles) was then added via syringe to the NaOH/ethanol solution and this allowed stirring for approximately 30 min. A solution containing bromo-[1,2-$^{13}$C$_2$]acetic acid (5 g, 0.035 moles), H$_2$O (50 ml), and sodium bicarbonate (3.27 g, 0.039 moles) was then added to the benzenethiol solution and the combined solution stirred for 1 hr. The solution was acidified with 6M HCl to pH=2.0 and extracted with portions of ethylacetate (3×200 ml). The combined organic layers were dried over sodium sulfate, filtered and solvent removed by rotary evaporation. Purification by chromatography on silica gel yielded phenylthio-[1, 2-$^{13}C_2$]acetic acid (compound 9 in FIG. 2) (4.87 g, 82%).

Example 3

The synthesis of ethyl phenylthio-[1,2-$^{13}C_2$]acetate (compound 14 in FIG. 3) was as follows. A round-bottom flask (500 ml) was fixed with a condenser cooled to 4° C. The flask was charged with a solution of phenylthio-[1,2-$^{13}C_2$]acetic acid (16.32 g, 0.096 mol), in dry ethanol (200 ml). Amberlyst®15 ion-exchange to the solution (7.0 g). The suspension was stirred using magnetic stirrer while heating to reflux (94° C.). The suspension was allowed to reflux for 6 hrs before cooling. When the solution has thoroughly cooled, the Amberlyst® was filtered off and the ethanol removed using a rotary evaporator. Extraction of the aqueous layer with portions of ethyl acetate (3×200 ml) and removal of the solvent (rotary evaporation) gave ethyl phenylthio-[1,2-$^{13}C_2$]acetate (14.73 g, 78%) as a brown viscous liquid.

Synthesis of ethyl (phenylsulfonyl)-[1,2-$^{13}C_2$]acetate (compound 15 in FIG. 3) was as follows. Oxone® (potassium peroxymonosulfate) (307 g, 0.255 moles) was dissolved in water (500 mL). Ethyl 2-(phenylthio)-[1,2-$^{13}C_2$]acetate (16.63 g, 0.085 moles) was dissolved in a mixture of ethyl acetate (100 mL) and ethanol (100 mL). This solution was added dropwise to the Oxone® solution over an hour. After the addition was complete, the reaction was stirred for an additional hour. The solution was then evaporated to remove most of the organic solvents. The aqueous layer was then extracted with portions of ethyl acetate (4×200 mL). The organic layer was dried over sodium sulfate, filtered and evaporated to give a quantitative yield of the ethyl (phenylsulfonyl)-[1,2-$^{13}C_2$]acetate (compound 15 in FIG. 3)

The synthesis of ethyl 2-[$^{13}C$]methyl-2-(phenylsulfonyl)-[1,2,3-$^{13}C_2$]propionate (compound 16 in FIG. 3) was as follows. Ethyl phenylsulfonyl-[1,2-$^{13}C_2$]acetate (0.5 g, 0.00217 moles) was suspended in dimethylformamide (15 ml) and allowed to stir for 15 m at room temperature. Solid potassium carbonate was added to the solution and allowed to stir for 1 hr at room temperature. Then [$^{13}C$]methyl iodide (0.713 g, 0.005 moles) was added to the solution. The round bottom flask capped tightly with a Teflon® stopper, and the reaction was allowed to proceed overnight. The product was isolated by filtering to remove the potassium carbonate precipitate. The filtrate was extracted with portions of ethyl acetate (3×50 ml). The combined organic layers were dried with sodium sulfate and the solvents removed by rotary evaporation. Residual DMF was removed in vacuo at 35-40° C. Ethyl 2-[$^{13}C$]methyl-2-(phenylsulfonyl)-[1,2,3-$^{13}C_3$]propionate was recovered as slightly yellow oil (0.46 g, 82%).

Figure 3:
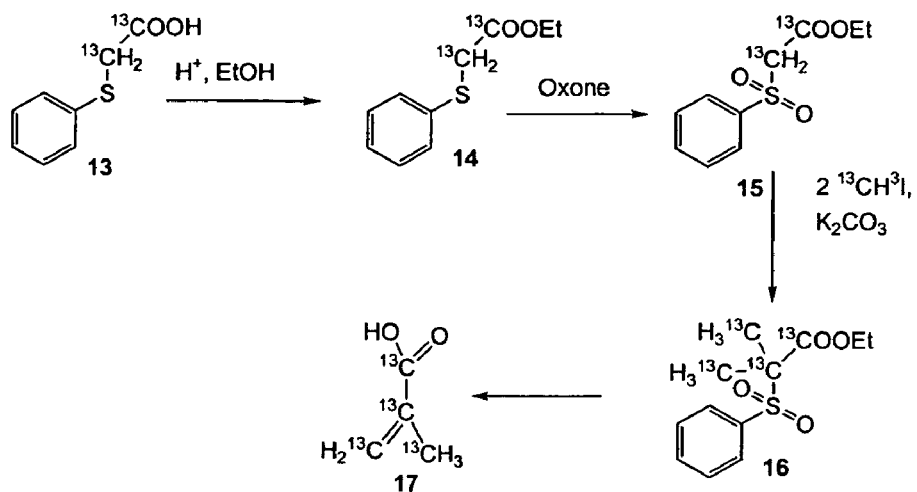
FIG. 3 shows a synthetic route to ethyl 2-[$^{13}$C]methyl-2-(phenylsulfonyl)-[1,2,3-$^{13}$C$_3$]propionate which could serve as a precursor to [$^{13}$C$_5$]methacrylic acid. This reaction sequence involves the intermediates phenylthio-[1,2-$^{13}$C$_2$] acetic acid, ethyl phenylthio-[1,2-$^{13}$C$_2$]acetate, and ethyl (phenylsulfonyl)-[1,2-$^{13}$C$_3$]acetate.

As diagrammed in FIG. 3, ethyl 2-[$^{13}C$]methyl-2-(phenylsulfonyl)-[1,2,3-$^{13}C_3$]propionate could serve as a precursor to [$^{13}C_5$]methacrylic acid.

Example 4

Figure 4:
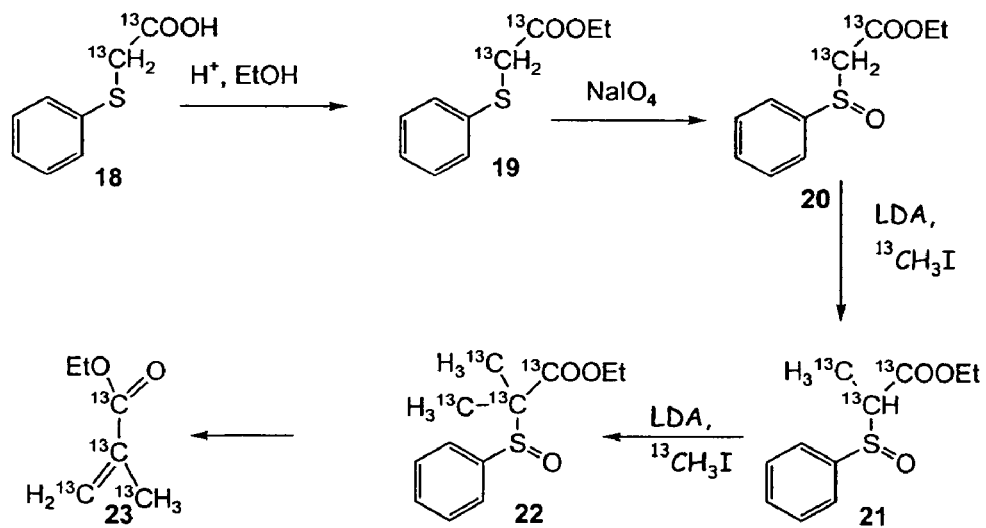
FIG. 4 shows a synthetic route to ethyl 2-[$^{13}$C]methyl-2-(phenylsulfinyl)-[1,2,3-$^{13}$C$_3$]propionate which could serve as a precursor to Ethyl [$^{13}$C$_5$]methacrylate (2-[$^{13}$C]methyl-2-[1,2,3-$^{13}$C$_3$]propenoic acid ethyl ester). This reaction sequence involves the intermediates phenylthio-[1,2-$^{13}$C$_2$]acetic acid, ethyl phenylthio-[1,2-$^{13}$C$_2$]acetate, ethyl (phenylsulfinyl)-[1,2-$^{13}$C$_3$]acetate, and ethyl 2-[$^{13}$C]methyl-2-(phenylsulfinyl)-[1,2,3-$^{13}$C$_3$]propionate

The synthesis of ethyl phenylthio-[1,2-$^{13}C_2$]acetate (compound 19 in FIG. 4) was as described in Example 3. Ethyl phenylsulfinyl-[1,2-$^{13}C_2$]acetate (compound 20 in FIG. 4) was prepared as follows. A 500 ml round-bottom flask was charged with a solution that contained ethyl phenylthio-[1, 2-$^{13}C_2$]acetate (10 g, 0.0505 moles) and 100 ml of a 50:50 mixture of methanol:$H_2O$ and was stirred using a magnetic stirrer. Sodium periodate (12.96 g, 0.0606 moles) was added to the solution and the reaction was stirred at room temperature for 24 h. The reaction mixture was then filtered to remove a white precipitate and methanol was removed from the filtrate using a rotary evaporator. The aqueous solution was extracted with portions of ethyl acetate (3×200 ml). The organic layer was dried over sodium sulfate, filtered and the solvent removed by rotary evaporation. Ethyl phenylsulfinyl-[1,2-$^{13}C_2$]acetate (compound 20 in FIG. 4) was recovered as a colorless oil (10.74 g, 99%).

Ethyl 2-phenylsulfinyl-[1,2,3-$^{13}C_3$]propionate (compound 21 in FIG. 4) was prepared as follows. A round bottom flask (250 ml) was charged with solution containing ethyl phenylsulfinyl-[1,2-$^{13}C_2$]acetate (5.0 g, 0.0233 mol), dissolved in dry tetrahydrofuran, and the solution was stirred under an argon atmosphere. The flask was cooled to −78° C. with a dry ice/ethanol bath. To the cooled solution, lithium diisopropylamine as a 1.5 M solution in cyclohexane (17.3 ml, 0.0257 mol) was added drop wise over 5 minutes. The reaction mixture was continually stirred at −78° C. for 1 hr. Then $^{13}CH_3I$ (3.50 g, 0.0245 mol) was added to the flask with a syringe and again the reaction was allowed to stir at −78° C. for 1 hr. Then the reaction was allowed to warm to room temperature and stirred for an additional 2 hrs. The reaction was quenched with the addition of a saturated ammonium chloride solution (50 ml). An aqueous solution of sodium thiosulfate was then added to consume residual $CH_3I$. The organic layer was extracted with portions of ethyl acetate (2×200 ml) and the ethyl acetate layer was washed with distilled water to remove ammonium chloride. The ethyl acetate layer was then dried over solid sodium sulfate, filtered and the solvent removed by rotary evaporation. The extraction gave ethyl 2-phenylsulfinyl-[1,2,3-$^{13}C_3$]propionate (compound 21 in FIG. 4) (5.44 g, 102%) as a clear-yellowish liquid.

Ethyl 2-[$^{13}C$]methyl-2-(phenylsulfinyl)-[1,2,3-$^{13}C_3$]propionate, (compound 22 in FIG. 4) was prepared as follows. A round bottom flask (250 ml) was charged with a solution containing ethyl 2-phenylsulfinyl-[1,2,3-$^{13}C_3$]propionate (1.5 g, 0.0065 moles) and freshly distilled tetrahydrofuran (22.5 ml). The solution was stirred with a magnetic stirrer placed under an argon atmosphere and cooled to −78° C. with a dry ice/ethanol bath. Using a syringe, lithium diisopropylamine as a 1.5 M solution in cyclohexane (4.8 ml, 0.00.0072 moles) was added drop wise over 5 minutes. After stirring the solution at −78° C. for 30 min, $^{13}CH_3I$ (0.983 g, 0.0069 mol) was added to the flask via syringe. The reaction was allowed to stir at −78° C. for 1 hr and then allowed to warm to room temperature. After stirring for an additional 2 hrs, the reaction was quenched with the addition of a saturated ammonium chloride solution (15 ml). An aqueous solution of sodium thiosulfate was then added to consume residual $CH_3I$. The organic layer was extracted with portions of ethyl acetate (2×200 ml) and the ethyl acetate layer was washed with distilled water to remove ammonium chloride. The ethyl acetate layer was then dried over solid sodium sulfate, filtered and the solvent removed by rotary evaporation. The extraction of the aqueous layer gave ethyl (1,2,3,4-$^{13}C_4$)-thiophenylbutanoate sulfoxide (1.59 g, 103%) to a clear-yellowish liquid. The extraction gave ethyl 2-[$^{13}C$]methyl-2-(phenylsulfinyl)-[1,2,3-$^{13}C_3$]propionate, (compound 22 in FIG. 4) as a clear-yellowish liquid (5.44 g, 102%).

Ethyl [$^{13}C_5$]methacrylate (2-[$^{13}C$]methyl-2-[1,2,3-$^{13}C_3$] propenoic acid ethyl ester) is preparable from ethyl 2-[$^{13}C$] methyl-2-(phenylsulfinyl)-[1,2,3-$^{13}C_3$]propionate (compound 22 in FIG. 4) in the manner described for the deuterated isotopomer (compound 7 in FIG. 1) of Example 1, i.e., by heating at a suitable temperature and pressure.

Although the present invention has been described with reference to specific details, it is not intended that such details should be regarded as limitations upon the scope of the invention, except as and to the extent that they are included in the accompanying claims.

The invention claimed is:

1. An isolated labeled compound of the formulae

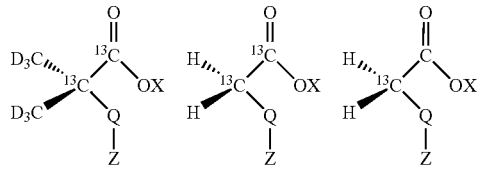

wherein Q is selected from the group consisting of —S(=O)—, and —S(=O)$_2$—, Z is an aryl group selected from the group consisting of 1-naphthyl, substituted 1-naphthyl, 2-naphthyl, substituted 2-naphthyl, and phenyl groups with the structure

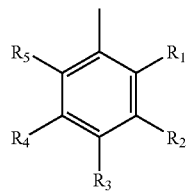

wherein $R_1$, $R_2$, $R_3$, $R_4$ and $R_5$ are each independently selected from the group consisting of hydrogen, a $C_1$-$C_4$ lower alkyl, a halogen, and an amino group selected from the group consisting of NH$_2$, NHR and NRR' where R and R' are each independently selected from the group consisting of a $C_1$-$C_4$ lower alkyl, an aryl group, and an alkoxy group, and X is selected from the group consisting of hydrogen, a $C_1$-$C_4$ lower alkyl group, and a fully-deuterated $C_1$-$C_4$ lower alkyl group.

2. An isolated labeled compound selected from the group of phenylthio-[1,2-$^{13}$C$_2$]acetic acid, phenylsulfinyl-[1,2-$^{13}$C$_2$]acetic acid, phenylsulfonyl-[1,2-$^{13}$C$_2$]acetic acid, ethyl phenylthio-[1,2-$^{13}$C$_2$]acetate, ethyl (phenylsulfonyl)-[1,2-$^{13}$C$_2$]acetate, 2-[$^2$H$_3$]methyl-2-(phenylsulfinyl)-[3,3,3-$^2$H$_3$]propionoic acid, methyl ester, ethyl 2-[$^{13}$C]methyl-2-(phenylsulfonyl)-[1,2,3-$^{13}$C$_2$]propionate, ethyl phenylsulfinyl-[1,2-$^{13}$C$_2$]acetate, ethyl 2-phenylsulfinyl-[1,2,3-$^{13}$C$_3$]propionate, and ethyl 2-[$^{13}$C]methyl-2-(phenylsulfinyl)-[1,2,3-$^{13}$C$_3$]propionate.

3. The isolated labeled compound of claim 1 wherein Q is —S(=O)— and X is hydrogen.

4. The isolated labeled compound of claim 1 wherein Q is —S(=O)$_2$— and X is hydrogen.

5. The isolated labeled compound of claim 1 wherein Q is —S(=O)— and X is C$^2$H$_3$.

6. The isolated labeled compound of claim 2 wherein the labeled compound is phenylthio-[1,2-$^{13}$C$_2$]acetic acid.

7. The isolated labeled compound of claim 3 wherein the labeled compound is phenylsulfinyl-[1,2-$^{13}$C$_2$]acetic acid.

8. The isolated labeled compound of claim 4 wherein the labeled compound is phenylsulfonyl-[1,2-$^{13}$C$_2$]acetic acid.

9. The isolated labeled compound of claim 2 wherein the labeled compound is ethyl phenylthio-[1,2-$^{13}$C$_2$]acetate.

10. The isolated labeled compound of claim 2 wherein the labeled compound is ethyl (phenylsulfonyl)-[1,2-$^{13}$C$_2$]acetate.

11. The isolated labeled compound of claim 5 wherein the labeled compound is 2-[$^2$H$_3$]methyl-2-(phenylsulfinyl)-[3,3,3-$^2$H$_3$]propionoic acid, methyl ester.

12. The isolated labeled compound of claim 2 wherein the labeled compound is ethyl 2-[$^{13}$C]methyl-2-(phenylsulfonyl)-[1,2,3-$^{13}$C$_2$]propionate.

13. The isolated labeled compound of claim 2 wherein the labeled compound is ethyl phenylsulfinyl-[1,2-$^{13}$C$_2$]acetate.

14. The isolated labeled compound of claim 2 wherein the labeled compound is ethyl 2-phenylsulfinyl-[1,2,3-$^{13}$C$_3$]propionate.

15. An isolated labeled compound of the formulae

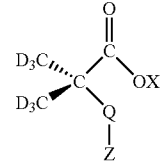

wherein Q is —S(=O)$_2$—, Z is an aryl group selected from the group consisting of 1-naphthyl, substituted 1-naphthyl, 2-naphthyl, and substituted 2-naphthyl, and X is selected from the group consisting of hydrogen, and a fully-deuterated $C_1$-$C_4$ lower alkyl group.

16. The isolated labeled compound of claim 2 wherein the labeled compound is ethyl 2-[$^{13}$C]methyl-2-(phenylsulfinyl)-[1,2,3-$^{13}$C$_3$]propionate.

* * * * *